US012636276B1

(12) United States Patent
Wang et al.

(10) Patent No.: US 12,636,276 B1
(45) Date of Patent: May 26, 2026

(54) METHODS AND COMPOSITIONS FOR TREATING HEMORRHOIDS

(71) Applicants: Jianmin Wang, Pelham, AL (US); Geping Cui, Beijing (CN)

(72) Inventors: Jianmin Wang, Pelham, AL (US); Geping Cui, Beijing (CN)

( * ) Notice: Subject to any disclaimer, the term of this patent is extended or adjusted under 35 U.S.C. 154(b) by 0 days.

(21) Appl. No.: 19/388,637

(22) Filed: Nov. 13, 2025

(51) Int. Cl.
| | |
|---|---|
| *A61K 31/4164* | (2006.01) |
| *A61K 9/02* | (2006.01) |
| *A61K 31/155* | (2006.01) |
| *A61K 31/4174* | (2006.01) |
| *A61P 9/14* | (2006.01) |

(52) U.S. Cl.
CPC ............ *A61K 31/4164* (2013.01); *A61K 9/02* (2013.01); *A61K 31/155* (2013.01); *A61K 31/4174* (2013.01); *A61P 9/14* (2018.01)

(58) Field of Classification Search
CPC .............. A61K 31/155; A61K 31/4164; A61K 31/4174; A61K 9/02; A61P 9/14
See application file for complete search history.

(56) References Cited

U.S. PATENT DOCUMENTS

| | | | | |
|---|---|---|---|---|
| 6,270,789 B1 * | 8/2001 | Sameshima | .............. | A61K 9/02 |
| | | | | 514/967 |
| 2015/0141881 A1 * | 5/2015 | Oh | ..................... | A61N 1/36007 |
| | | | | 607/3 |
| 2022/0362247 A1 | 11/2022 | Barannikov | | |
| 2023/0338309 A1 * | 10/2023 | Bouhadir | ................ | A61P 17/00 |

FOREIGN PATENT DOCUMENTS

| | | |
|---|---|---|
| CN | 11977571 C | 4/2005 |

OTHER PUBLICATIONS

Nicholson et al., "Topical Metronidazole (10 Percent) Decreases Posthemorrhoidectomy Pain and Improves Healing," Dis Colon Rectum 2004; 47: 711-16. (Year: 2004).*
Khan et al., "Formulation and Evaluation of Mucoadhesive in-Situ Rectal Gel of Clotrimazole," World J. Pharma. Res. 12(18), 701-09 (2023). (Year: 2023).*
Ignite Healthwise, LLC Staff. "Infrared Photocoagulation for Internal Hemorrhoids: Before Your Procedure" https://healthy. kaiserpermanente.org/health-wellness/health-encyclopedia/he.infrared-photocoagulation-for-internal-hemorrhoids-before-your-procedure. abk7009 published on Oct. 6, 2025.
Cleveland Clinic. "Sitz Bath". https://my.clevelandclinic.org/health/ treatments/24137-sitz-bath published on Sep. 11, 2022.
Preparation H. "Rapid Relief Spray with Lidocaine." https://www. preparationh.com/products/rapid-relief-spray-with-lidocaine pub-lished on Jul. 22, 2024.
ISR/WO for PCT/US25/55372 issued on Mar. 30, 2026.

* cited by examiner

*Primary Examiner* — Theodore R. Howell
(74) *Attorney, Agent, or Firm* — Rhodes IP PLC; Christopher R Rhodes

(57) ABSTRACT

A method of using a pharmaceutical composition compris-ing metronidazole, clotrimazole and chlorhexidine for treat-ing patients suffering from hemorrhoids, is disclosed. The mixture of metronidazole, clotrimazole and chlorhexidine can be applied to contact the hemorrhoids to relieve and/or reduce the symptoms caused by the hemorrhoids. Various application forms including solid forms and solution forms of the mixture of compounds can be used to treat the hemorrhoids.

13 Claims, 1 Drawing Sheet

METHODS AND COMPOSITIONS FOR TREATING HEMORRHOIDS

TECHNOLOGICAL FIELD

The invention relates to the field of practical medicine, namely, to pharmaceutical compositions and the use of the pharmaceutical compositions to treat hemorrhoids.

BACKGROUND

Hemorrhoids are swollen and enlarged veins in the lower rectum and anus and can cause significant pain, itching and bleeding.

SUMMARY

Various aspects, embodiments and features are described of methods and compositions for treating hemorrhoids.

In an aspect, a method comprises administering a pharmaceutical composition to a patient with a hemorrhoid for relieving hemorrhoidal symptoms and eliminating hemorrhoidal swelling, itching, pain, bleeding, and inflammation so the administered pharmaceutical composition contacts the hemorrhoid.

In certain embodiments, the pharmaceutical composition comprises a combination of metronidazole, clotrimazole, and chlorhexidine.

In some embodiments, the metronidazole, is present in the pharmaceutical composition, and is present in the pharmaceutical composition in an amount of about 10% to about 30% weight based on the total weight of the pharmaceutical composition.

In other embodiments, the clotrimazole is present in the pharmaceutical composition, and is present in the pharmaceutical composition in an amount of about 10% to about 20% weight based on the total weight of the pharmaceutical composition.

In some embodiments, chlorhexidine is present in the pharmaceutical composition, and is present in the pharmaceutical composition in an amount of about 0.1% to about 1% weight based on the total weight of the pharmaceutical composition. The chlorhexidine can be present in various forms including, for example, acetate, diacetate, hydrochloride or other forms.

In certain embodiments, the metronidazole is present in the pharmaceutical composition in an amount in the range of about 200 mg to about 300 mg, the clotrimazole is present in the pharmaceutical composition in an amount in the range of about 100 mg to about 200 mg, and the chlorhexidine is present in the pharmaceutical composition in an amount in the range of about 1.0 mg to about 10.0 mg.

In some embodiments, the pharmaceutical composition is formulated as a suppository pharmaceutical dosage form.

In certain embodiments, the pharmaceutical composition is administered once or twice a day or once every 2 or 3 or 4 days to the patient in a suppository pharmaceutical dosage form.

In other embodiments, the pharmaceutical composition is administered for a period of at least 1 week.

In certain embodiments, the pharmaceutical composition is formulated as an enema pharmaceutical dosage form.

In some embodiments, the pharmaceutical composition is dissolved in a solution prior to contact administration of the pharmaceutical composition to treat the hemorrhoid.

In certain embodiments, the method comprises pre-heating of the hemorrhoid prior to administration of the pharmaceutical composition.

In some embodiments, the pre-heating comprises exposure of the hemorrhoid to infrared light.

In other embodiments, the pre-heating comprises exposure of the hemorrhoid to water at a temperature above a body temperature of the patient.

In certain embodiments, the method comprises administering the composition to the patient in both a solid form and in a liquid form. In some embodiments, the solid form is formulated as a suppository pharmaceutical dosage form. In other embodiments, the liquid form is formulated as an enema pharmaceutical dosage form.

In another aspect, a pharmaceutical composition for relieving hemorrhoidal symptoms and eliminating hemorrhoidal swelling, itching, pain, bleeding, and inflammation by contact of the hemorrhoid with the pharmaceutical composition comprises a synergistic combination of metronidazole, clotrimazole and chlorhexidine. In some embodiments, the metronidazole is present in the pharmaceutical composition in an amount of about 10% to about 30% weight based on the total weight of the pharmaceutical composition, the clotrimazole is present in the pharmaceutical composition in an amount of about 10% to about 20% weight based on the total weight of the pharmaceutical composition, and the chlorhexidine is present in the pharmaceutical composition in an amount of about 0.1% to about 1% weight based on the total weight of the pharmaceutical composition.

In certain embodiments, the pharmaceutical composition is formulated as a suppository or a cream.

In other embodiments, the pharmaceutical composition is formulated as an enema.

In additional embodiments, the metronidazole is present in the pharmaceutical composition in an amount in the range of about 200 mg to about 300 mg, the clotrimazole is present in the pharmaceutical composition in an amount in the range of about 100 mg to about 200 mg, and the chlorhexidine is present in the pharmaceutical composition in an amount in the range of about 1.0 mg to about 10.0 mg.

In some embodiments, the pharmaceutical composition is formulated in a solid form for application onto a surface of the hemorrhoid to contact the hemorrhoid.

In other embodiments, the pharmaceutical composition is formulated as a solution or aerosol for spraying onto a surface of the hemorrhoid to contact the hemorrhoid.

In additional embodiments, the pharmaceutical composition is present in both a solid form and as a solution, and wherein each of the solid form and the solution form can be applied to a surface of the hemorrhoid to contact the hemorrhoid.

Additional features, aspects and embodiments are described in more detail below.

BRIEF DESCRIPTION OF THE SEVERAL VIEWS OF THE DRAWINGS

FIG. 1 shows a chemical structure of metronidazole; and

FIG. 2 shows a chemical structure of clotrimazole; and

FIG. 3 shows a chemical structure of chlorhexidine.

DETAILED DESCRIPTION

Various aspects, features, embodiments, examples and configurations of the invention relate to the field of practical medicine, namely, to the use of pharmaceutical compositions for alleviating manifestations of hemorrhoids. For example, various aspects relate to use of a combination of metronidazole, clotrimazole and chlorhexidine to treat hemorrhoids including, for example, fully internal hemorrhoids, fully external hemorrhoids and prolapsing hemorrhoids.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Hemorrhoids are believed to develop when the venous drainage of the anus is altered, causing the venous plexus and connecting tissue to dilate, creating an outgrowth of anal mucosa from the anorectal wall. However, the exact pathophysiology is unknown. Hemorrhoids occur above or below the dentate line where the proximal columnar transitions to the distal squamous epithelium. Hemorrhoids are common. The exact prevalence is unknown because most patients are asymptomatic and do not seek care from a physician. Studies show that patients undergoing routine colorectal cancer screening to be found a 39% prevalence of hemorrhoids, with 55% of those patients reporting no symptoms. Hemorrhoids are more prevalent in persons 45 to 65 years of age. The precise cause is not well understood, but hemorrhoids are associated with conditions that increase pressure in the hemorrhoidal venous plexus, such as straining during bowel movements secondary to constipation. Other associations include obesity, pregnancy, chronic diarrhea, anal intercourse, cirrhosis with ascites, pelvic floor dysfunction, and a low-fiber diet. Conservative treatments of hemorrhoids consist of a high-fiber diet, fiber supplementation, increased water intake, warm water baths, and stool softeners. There are many topical over-the-counter hemorrhoid remedies. These may provide temporary relief, such as these include astringents, protectants, decongestants, corticosteroids, and topical anesthetics. Over-the-counter hemorrhoid preparations often combine two or more of these ingredients. Office-based and surgical procedures can effectively treat hemorrhoids refractory to medical therapies. In general, the lower the grade, the more likely an office-based procedure will be successful, whereas recurring and grade III or IV hemorrhoids are more amenable to excisional hemorrhoidectomy.

Metronidazole, a synthetic nitroimidazole antibiotic, is taken into cells by passive diffusion, and the nitro side chain on the imidazole ring is reduced intracellularly by the pyruvate-ferredoxin reductase complex into a toxic nitro radical that reacts with DNA, leading to DNA strand breaks, helix destabilization, and ultimately cell death in both dividing and nondividing cells. Metronidazole demonstrates concentration-dependent bactericidal activity. One of the major metabolites, a hydroxy derivative, retains significant antibiotic activity. Metronidazole is active against anaerobic bacteria. In addition to direct bactericidal activity, metronidazole also appears to have direct effects on decreasing neutrophil generation of hydrogen peroxide and hydroxyl radicals, which may lead to decreased inflammation at the site of infection. Given the excellent tissue penetration characteristics of metronidazole, activity against all susceptible anaerobes is achievable in most tissue sites. Metronidazole was reported in management of post-open haemorrhoidectomy pain, but there is no recommendation in clinical settings that metronidazole be used in the management of post-open haemorrhoidectomy pain because there is insufficient evidence to support the effectiveness.

Chlorhexidine, e.g., chlorhexidine acetate or chlorhexidine hydrochloride, is a widely used antiseptic agent that has found applications in various medical and dental contexts. Its effectiveness against a broad spectrum of microorganisms, including bacteria, fungi, and some viruses, makes it a staple in infection control. The primary mechanism of action of chlorhexidine hydrochloride involves disruption of the microbial cell membrane. Chlorhexidine molecules are cationic, meaning they carry a positive charge. When they encounter the cell walls of bacteria, which are typically negatively charged, electrostatic interactions occur. These interactions cause the Chlorhexidine molecules to bind to the microbial cell wall. Once bound to the cell wall, Chlorhexidine Hydrochloride exerts its lethal effect by causing the cell membrane to lose its integrity. Chlorhexidine Hydrochloride also has a residual effect, particularly on skin and mucous membranes. When applied, it binds to proteins found in the skin or mucous tissues, creating a reservoir of the antiseptic agent. This binding allows Chlorhexidine to continue exerting its antimicrobial effect long after the initial application, providing prolonged protection against microbial colonization. The efficacy of Chlorhexidine Hydrochloride is also influenced by its concentration and formulation. At lower concentrations, it acts as a bacteriostatic agent, inhibiting the growth and reproduction of bacteria. At higher concentrations, it has a bactericidal effect, leading to the destruction of bacterial cells. Its broad-spectrum activity includes effectiveness against Gram-positive and Gram-negative bacteria, as well as some fungi and viruses. This broad antimicrobial activity makes it an invaluable tool in preventing infections, particularly in surgical and hospital environments where the risk of infection is high.

Clotrimazole is a synthetic imidazole with a broad spectrum of antimycotic activity. Clotrimazole is an FDA-approved drug to treat oral candidiasis, vulvovaginal candidiasis, and dermatomycoses. This drug is an effective treatment for skin infections such as athlete's foot, jock itch, ringworm, *Pityriasis versicolor*, intertrigo, and erythrasma. Clotrimazole exerts its action primarily by damaging the permeability barrier in the fungal cytoplasmic membrane. Clotrimazole inhibits the biosynthesis of ergosterol in a concentration-dependent manner by inhibiting the demethylation of 14-α-lanosterol. When ergosterol synthesis becomes inhibited, the cell can no longer construct an intact and functional cell membrane. Ergosterol also directly promotes the growth of fungal cells in a hormone-like fashion; therefore, the rapid onset of these events leads to a dose-dependent inhibition of fungal growth. Additionally, clotrimazole has some activity against certain gram-positive bacteria and, at very high concentrations, has activity against *Trichomonas* spp. In adults and children older than 12, the FDA has approved the use of clotrimazole in combination with betamethasone propionate (corticosteroid) for the topical treatment of inflammatory tinea.

Certain formulations described herein use a combination of materials in the field of practical medicine, namely, for alleviating manifestations of hemorrhoids. While prior treatment of vaginal infections has used a combination of chlorhexidine, clotrimazole, and metronidazole, studies show that chlorhexidine vaginal gel is more effective in treatment of vaginal infections than a combination therapy of chlorhexidine, clotrimazole, and metronidazole. This invention demonstrates that the combination of chlorhexidine, clotrimazole, and metronidazole is effective as a treatment of hemorrhoids as it can eliminate itching, inflammation, swelling and pain. Various compositions and methods have previously been developed which generally relieve either the itching or inflammation, but few have been successful in reducing or completely eliminating swelling, itching and inflammation. In this invention, various aspects relate to a method of use of a combination of metronidazole, clotrimazole and chlorhexidine to treat hemorrhoids.

Therefore, a unique combination of metronidazole, clotrimazole and chlorhexidine would potentially be, in terms of working through multi-mechanisms of actions, more effective in the treatment of hemorrhoids.

In an aspect, the technology described herein is directed to a method of a preparation for use in the treatment of hemorrhoids by eliminating one or more of swelling, itching, inflammation, bleeding and pain attributable to hemorrhoids. For example, a method is presented of preparing the combination of metronidazole, clotrimazole and chlorhexidine for contact application, e.g., topical applications, to the anorectal area to eliminate the above-mentioned swelling, itching, inflammation, bleeding and pain. Depending on the specific symptoms, the administration can be on any or all the regions of the anorectal area including the perianal area or portion of the skin and buttocks immediately surrounding the anus, anal skin area of the anal canal, and the mucous membrane of the rectum. For example, the combination of metronidazole, clotrimazole and chlorhexidine is applied topically to the involved area until the symptoms are eliminated. For example, the combination of metronidazole, clotrimazole and chlorhexidine is applied topically to the involved area causing hemorrhoids once or several times a day.

In certain aspects, the combination of metronidazole, clotrimazole and chlorhexidine can be administered to the patient with hemorrhoids in a suppository or gel or cream or ointment form suitable for anorectal administration or perianal area administration. For example, a suppository form can be made with weight 10% metronidazole, 5% clotrimazole, 1% chlorhexidine, 60% Polyethylene Glycol 6000, 20% Polyethylene Glycol 1500, and 4% Polyethylene Glycol. An ointment can be made with weight 5% metronidazole, 3.5% clotrimazole, 1.5% chlorhexidine, 7% Steric acid 2% Cetyl alcohol, 20% Mineral Oil, 10% Glycerin, and Purified water to balance the formulation. The formulations described herein are intended to treat both external and internal hemorrhoids, and the exact form and delivery mechanism used can vary depending on the particular location of the hemorrhoid(s) to be treated.

The present invention includes a method of treating hemorrhoids with a pharmaceutical composition that comprises three pharmaceutically active ingredients, metronidazole, clotrimazole, and chlorhexidine as a form of ointment or cream or suppository for anal or anorectal area administration.

The present invention includes a method of treating hemorrhoids with a pharmaceutical composition that comprises three pharmaceutically active ingredients, metronidazole, clotrimazole, and chlorhexidine in a solution mixture to contact an anal or anorectal area administration.

In some embodiments of this invention, metronidazole in the pharmaceutical composition for treating hemorrhoids is provided in an amount of about 100 mg to about 300 mg or 15%-30% weight, clotrimazole in an amount of about 100 mg to about 200 mg or 10%-20% weight and chlorhexidine in an amount of about 1 mg to about 10 mg or 0.1%-1% weight. The exact dosage used can depend, for example, on the particular form of the composition used and/or the location of the hemorrhoid.

In some embodiments of this invention, a suppository pharmaceutical dosage form of the pharmaceutical composition containing metronidazole in an amount of about 250 mg or 25% % weight, clotrimazole in an amount of about 100 mg or 10% weight and chlorhexidine in an amount of about 10 mg or 1% weight to be administered to patients with hemorrhoids.

Aspect 1 is a method comprising administering a pharmaceutical composition to a patient having hemorrhoids; wherein the pharmaceutical composition comprises effective amounts of metronidazole, clotrimazole and chlorhexidine; and wherein the effective amounts together are sufficient to treat the patient with hemorrhoid disorder.

Aspect 2 is the method of Aspect 1, wherein the pharmaceutical composition is administered once or twice a day, or once every 2 or 3 or 4 days to the patient in an solid form or a gel form or a solution form.

Aspect 3 is the method of any of Aspects 1-2, wherein the metronidazole is present in the pharmaceutical composition in an amount in the range of about 10% to about 30% weight.

Aspect 4 is the method of any of Aspects 1-3, wherein the clotrimazole is present in the pharmaceutical composition in an amount in the range of about 10% to about 20% weight.

Aspect 5 is the method of any of Aspects 1-4, wherein the chlorhexidine is present in the pharmaceutical composition in an amount in the range of about 0.1% to about 1% weight.

Aspect 6 is the pharmaceutical composition of any of Aspects 1-5, wherein the pharmaceutical composition is formulated as a solid pharmaceutical dosage form.

Aspect 7 is the pharmaceutical composition of any of Aspects 6, wherein the solid pharmaceutical dosage form is a suppository form.

In another aspect, use of a combination of metronidazole, clotrimazole and chlorhexidine to treat hemorrhoids is described. In certain embodiments, the use includes administration of the combination of metronidazole, clotrimazole and chlorhexidine once or twice a day, or once every 2 or 3 or 4 days to the patient in a suppository form. In certain embodiments, the use includes administration of the combination of metronidazole, clotrimazole and chlorhexidine once or twice a day, or once every 2 or 3 or 4 days to the patient in a solution form, e.g., by dissolving pre-combined mixtures of the compounds into a sitz bath, using an enema containing the drug mixture or other devices which can apply the liquid to the affected hemorrhoid. In other embodiments, the use includes administration of the metronidazole is present in the pharmaceutical composition in an amount in the range of about 10% to about 30% weight. In some embodiments, the use includes administration of the clotrimazole in the pharmaceutical composition in an amount in the range of about 10% to about 20%. In some embodiments, the use includes administration of the chlorhexidine in the pharmaceutical composition in an amount in the range of about 0.1% to about 1% weight. In additional embodiments, the use includes administration of the pharmaceutical composition as a solid pharmaceutical dosage form. In other embodiments, the use includes administration of the solid pharmaceutical dosage form is a suppository form.

Through clinical practices, the inventors of the present invention found that a pharmaceutical composition with solid or gel or cream dosage forms comprising the active agents, metronidazole, clotrimazole and chlorhexidine, is suitable for treating patients suffering from hemorrhoids. The mixture of metronidazole, clotrimazole and chlorhexidine can also be applied in solution form either by spray, enema or by way of a sitz bath to permit absorption of the mixture into the hemorrhoid(s).

The methods and compositions described herein can be used in combination with other treatments including pre-soaking of the hemorrhoids in a sitz bath optionally including salts or other materials. In other instances, the methods and compositions described herein can be used in combination with infrared light exposure therapy, cauterization or other treatments. Further, topical steroids, anti0finalmatries Definitions As used in the present specification, the following words and phrases are generally intended to have the meanings as set forth below, except to the extent that the context in which they are used indicates otherwise.

As used herein, the term "metronidazole" refers to 2-(2-methyl-5-nitro-1H-imidazol-1-yl)ethanol and is an imidazole substituted at the 1, 2 and 5 positions with 2-hydroxy-ethyl, nitro and methyl groups, respectively, as shown in FIG. 1.

As used herein, the term "clotrimazole" refers to 1-[(2-chlorophenyl)-diphenylmethyl]imidazole and is a 1H-imidazole in which the hydrogen attached to a nitrogen is replaced by a monochlorotrityl group as shown in FIG. 2.

As used herein, the term "chlorhexidine" refers to (1E)-2-[6-[[amino-[(E)-[amino-(4-chloroanilino)methylidene]amino]methylidene]amino]hexyl]-1-[amino-(4-chloroanilino)methylidene]guanidine and is a structure consisting of two (p-chlorophenyl)guanide units linked by a hexamethylene bridge as shown in FIG. 3.

As used herein, "treating" or "treatment" means complete cure or incomplete cure, or it means that the symptoms of the underlying disease or associated conditions are at least reduced and/or delayed, and/or that one or more of the underlying cellular, physiological, or biochemical causes or mechanisms causing the symptoms are reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is sufficient to affect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutical compositions may be administered in either single or multiple doses by anorectal administration. Administration may be by way of any one or more of suppository, cream, gel, spray, drops, solution, suspensions, syrups, or the like.

The term "about" used herein in the context of quantitative measurements means the indicated amount ±10%. For example, with a ±10% range, "about 2 mg" can mean 1.8-2.2 mg.

The pharmaceutical compositions may be formulated for pharmaceutical use using methods known in the art, for example, Ansel's Pharmaceutical Dosage Forms and Drug Delivery Systems Tenth (by Loyd Allen, 2013) and Handbook of Pharmaceutical Manufacturing Formulations (Volumes 1-6 by Sarfaraz K. Niazi). Accordingly, incorporation of the active compounds and a controlled, or slow release matrix may be implemented.

Either fluid or solid unit dosage forms can be readily prepared for anorectal or anorectal area administration, for example, admixed with any one or more of conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent subjects sustained release formulations may even be preferred. Suppository may be formulated by mixing the pharmaceutical composition with a pharmaceutical diluent which is inert and inserting this mixture into a hard gelatin capsule having the appropriate size. If soft suppository are desired, a slurry of the pharmaceutical composition with an acceptable vegetable, light petroleum or other inert oil can be encapsulated by forming into a gelatin suppository.

Suspensions, syrups, enemas and elixirs may be used for anorectal administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or other non-nutritive sweetener, and/or a biological sweetener and/or a flavoring agent, such as in the form of an elixir.

The solid dosage formulation of this disclosure means a form of suppository, caplets, bi-layer suppository, film-coated suppository, or the like. Suppositories in accordance with this disclosure can be prepared by any mixing and forming techniques that are well known in the pharmaceutical formulation industry. In some examples, the dosage formulation is fabricated by direct compressing the respectively prepared sustained-release portion and the immediate-release portion by punches and dies fitted to a rotary forming press, ejection or compression molding or granulation followed by compression.

The pharmaceutical compositions provided in accordance with the present disclosure can be typically administered topically or in some manner where the active compounds can contact the affected hemorrhoid. This disclosure therefore provides pharmaceutical compositions that comprise a solid dispersion comprising metronidazole, clotrimazole and chlorhexidine as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical arts (see, e.g., Ansel's Pharmaceutical Dosage Forms and Drug Delivery Systems, Tenth (by Loyd Allen, 2013) and Handbook of Pharmaceutical Manufacturing Formulations (Volumes 1-6 by Sarfaraz K. Niazi)).

The pharmaceutical compositions may further comprise pharmaceutical excipients such as diluents, binders, fillers, glidants, disintegrants, lubricants, solubilizers, and combinations thereof. Some examples of suitable excipients are described herein. When the pharmaceutical compositions are formulated into suppositories, suppositories may be uncoated or may be coated by known techniques including microencapsulation to delay disintegration and absorption in the gastrointestinal tract and thereby provide a sustained action over a longer period. For example, a time delay material such as glyceryl monostearate or glyceryl distearate alone or with a wax may be employed. In embodiments, the pharmaceutical compositions are formulated as tablets, caplets, pills, or capsules for gastrointestinal absorption, such as formulated to be capable of delaying disintegration until the pharmaceutical composition is in the gastrointestinal tract of a patient. In embodiments, delaying disintegration is achieved using a coating.

In embodiments, the pharmaceutical compositions can comprise synergistically effective amounts of metronidazole, clotrimazole and chlorhexidine, such as a) about 10% to 30% weight of metronidazole, b) about 10% mg to 20% weight of clotrimazole and c) about 0.1% mg to 1% weight of chlorhexidine; a) about 15% to 20% weight of metronidazole, b) about 10% mg to 15% weight of clotrimazole and c) about 0.2% mg to 0.5% weight of chlorhexidine; a) about 20% to 25% weight of metronidazole, b) about 10% mg to 12% weight of clotrimazole and c) about 0.2% mg to 0.5% weight of chlorhexidine. In embodiments, the metronidazole is present in the pharmaceutical composition in a synergistically effective amount relative to the amount of clotrimazole and chlorhexidine and can include pharmaceutical compositions comprising a) about up to and including any of 10%, 15%, 20%, 25%, 30% weight or any amount within any of these ranges, b) about up to and including any of between 10%, 12%, 14%, 16%, 18%, 20% weight clotrimazole, and c) about up to and including any of between 0.1%, 0.2%, 0.4%, 0.6%, 0.8%, 1.0% weight chlorhexidine. Together, the synergistically effective amounts can be used to treat the hemorrhoids.

The exact forms of the metronidazole, clotrimazole and chlorhexidine used in the various formulations herein can vary. For example, metronidazole is typically used as hydrochloride or sodium salt or in a solution of sodium chloride. Clotrimazole is weak base and may be used in its natural state or as a salt, e.g., maleic acid salt, adipic acid salt, etc. to enhance its absorption and/or water solubility. Chlorhexidine is typically used as a salt including an acetate salt, a diacetate salt, a digluconate salt, a bis(guanide) salt, or a dihydrochloride salt. Depending on the exact pH of the mixture including the metronidazole, clotrimazole and chlorhexidine, the form of each compound in the solid or liquid treatment form may vary.

The pharmaceutical compositions, pharmaceutical dosage forms, and suppository containing metronidazole, clotrimazole and chlorhexidine as described herein are administered to a patient suffering from hemorrhoids, by administration (such as anorectal administration) once daily, twice daily, up to four times a day, once every other day, once a week, two times a week, three times a week, four times a week, or five times a week, or combinations thereof.

In embodiments, the pharmaceutical dosage forms and suppositories of pharmaceutical compositions containing metronidazole, clotrimazole and chlorhexidine as described herein are effective in reversing, reducing, alleviating, and/or treating one or more symptoms of hemorrhoids, such as swelling, itching, pain, bleeding, inflammation, in about 1-8 weeks, such as within 1, 2, 3, 4, 5, 6, 7, or 8 weeks, or any range in between.

In certain embodiments, the pharmaceutical compositions described herein can be used in combination with heating of the hemorrhoids to increase the absorption and/or effectiveness of the pharmaceutical composition. Heating can be accomplished, for example, using infrared radiation or heat transfer from heated water or heated devices placed in contact with the hemorrhoid. The use of infrared light may also shrink the size of hemorrhoids to at least some degree, which permits use of the infrared light in combination with the pharmaceutical composition to treat grade 1-4 hemorrhoids including fully internal hemorrhoids, fully external hemorrhoids and prolapsing hemorrhoids. In the case of infrared light application, the light can be applied for a short period heat the hemorrhoid but avoid coagulation of the hemorrhoid or can be applied for a sufficient period to coagulate at least some portion of the hemorrhoid. Application of the pharmaceutical composition can follow the application of the heat, or the pharmaceutical composition can be applied prior to heating to enhance post-application absorption of the pharmaceutical composition.

The following Examples are illustrative and should not be interpreted to limit the scope of the claimed subject matter.

Example 1

A 65-year-old female patient was diagnosed with internal hemorrhoids with painless bright red bleeding, prolapse, soiling, mild grape-like tissue prolapses, and itching. The patient went through various of treatments over a course of two years, including a high-fiber diet, warm water baths, stool softeners, topical nitroglycerin (0.4%), and use of a topical metronidazole cream with 10% metronidazole. With no relief from any of those treatments, her symptoms persisted. Then the patient was treated with a suppository including a combination of metronidazole (20% by weight based on the overall weight of the suppository formulation), clotrimazole (15% by weight based on the overall weight of the suppository formulation), and chlorhexidine (0.3% by weight based on the overall weight of the suppository formulation) twice a day for two weeks. She experienced no more bleeding, soiling and itching and the swelling was reduced by 50% by the end of the two weeks of treatment.

Example 2

A 55-year-old male patient was diagnosed with external hemorrhoids with his anal area showing moderate swelling and light bleeding. He complained of pain, itching or irritation in the anal area. He tried high fiber diets and warm baths regularly. His symptoms showed no improvement. He also tried a hemorrhoid cream containing hydrocortisone, a topical cream containing 10% metronidazole, and a suppository containing hydrocortisone over a year. These treatments only provided temporary relief to him. Then, he was treated with a suppository of the combination of metronidazole (20% weight based on the overall weight of the suppository formulation), clotrimazole (15% weight based on the overall weight of the suppository formulation), and chlorhexidine (0.3% weight based on the overall weight of the suppository formulation) twice a day for two weeks. At the end of the treatment, he had mild swelling but no bleeding, pain, itching or irritation in the anal area.

Example 3

A 47-year-old male patient was diagnosed with both internal and external hemorrhoids He complained of bleeding during bowel movements, persistent pain and itching in the anal area during daytime. Over a period of 6 months, the patient tried various sequential treatment such as a cream with hydrocortisone, chlorhexidine 4% ointment, a cream with lidocaine, and a suppository containing hydrocortisone. None of those treatments eliminated his symptoms for more than a week without daily administration of any of them. Then he was prescribed with the suppository of the combination of metronidazole (20% weight based on the overall weight of the suppository formulation), clotrimazole (15% weight based on the overall weight of the suppository formulation), and chlorhexidine (0.3% weight based on the overall weight of the suppository formulation) twice a day for two weeks. At the end of the treatment, he no bleeding, pain, or itching in the anal area. Even after 2 months post-treatment, he had no complaints of any of bleeding, pain, or itching.

REFERENCES

Fox A, Tietze P H, Ramakrishnan K. Anorectal conditions: hemorrhoids. FP Essentials. 2014; 419:11-19.

Kaidar-Person O, Person B, Wexner S D. Hemorrhoidal disease: A comprehensive review. J Am Coll Surg. 2007; 204:102-117.

Varut Lohsiriwat. Hemorrhoids: From basic pathophysiology to clinical management. World J. Gastroenterol. 2012 May 7; 18 (17).

Guy R J, Seow-Choen F. Septic complications after treatment of haemorrhoids. Br J Surg 2003; 90:147-156. doi: 10.1002/bjs.4008.

Tjandra J J, Tan J J, Lim J F, Murray-Green C, Kennedy M L, Lubowski D Z. Rectogesic (glyceryl trinitrate 0.2%) ointment relieves symptoms of haemorrhoids associated with high resting anal canal pressures. Colorectal Dis. 2007; 9:457-463.

Johanson J F. Nonsurgical treatment of hemorrhoids. J Gastrointest Surg. 2002; 6:290-294.

Moesgaard F, Nielsen M L, Hansen J B, Knudsen J T. High-fiber diet reduces bleeding and pain in patients with hemorrhoids: a double-blind trial of Vi-Siblin. Dis Colon Rectum. 1982; 25:454-456.

Alonso-Coello P, Mills E, Heels-Ansdell D, López-Yarto M, Zhou Q, Johanson J F, Guyatt G. Fiber for the treatment of hemorrhoids complications: a systematic review and meta-analysis. Am J Gastroenterol. 2006; 101:181-188.

Löfmark S, Edlund C, Nord C E. Metronidazole is still the drug of choice for treatment of anaerobic infections. Clin Infect Dis. 2010 Jan. 1; 50.

Metronidazole, Drug Usage Statistics, United States, 2014-2023

Freeman C D, Klutman N E, Lamp K C (November 1997). "Metronidazole. A therapeutic review and update". Drugs. 54(5):679-708.

Woo T E, Somayaji R, Haber R M, Parsons L. Diagnosis and Management of Cutaneous Tinea Infections. Adv Skin Wound Care. 2019 August; 32(8):350-357.

Sawyer P R, Brogden R N, Pinder R M, Speight T M, Avery Clotrimazole: a review of its antifungal activity and therapeutic efficacy. Drugs. 1975; 9(6):424-47.

Haller I. Mode of action of clotrimazole: implications for therapy. Am J Obstet Gynecol. 1985 Aug. 1; 152(7 Pt 2):939-44.

Crowley P D, Gallagher H C. Clotrimazole as a pharmaceutical: past, present and future. J Appl Microbiol. 2014 September; 117(3):611-7.

Łukomska-Szymańska M, Sokołowski J, Łapińska B. Chlorhexidine—mechanism of action and its application to dentistry. J Stomatol. 2017; 70:405-417.

Lim, K. S. and P. A. A. Kam. "Chlorhexidine—pharmacology and Clinical Applications." Anaesthesia and Intensive Care 36.4 (2008).

Milstone, Aaron M., Catherine L. Passaretti and Trish M. Perl. "Healthcare Epidemiology: Chlorhexidine: Expanding the Armamentarium for Infection Control and Prevention." Clinical Infectious Diseases 46.2 (2008): 274-81

Loyd Allen, Ansel's Pharmaceutical Dosage Forms and Drug Delivery Systems, Tenth (2013).

Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

What is claimed is:

1. A method comprising:
administering a pharmaceutical composition to a patient with a hemorrhoid for relieving hemorrhoidal symptoms and eliminating hemorrhoidal swelling, itching, pain, bleeding, and inflammation so the administered pharmaceutical composition contacts the hemorrhoid;
wherein the pharmaceutical composition comprises a combination of metronidazole, clotrimazole, and chlorhexidine;
wherein the metronidazole is present in the pharmaceutical composition in an amount in a range of about 200 mg to about 300 mg;
wherein the clotrimazole is present in the pharmaceutical composition in an amount in a range of about 100 mg to about 200 mg; and
wherein chlorhexidine is present in the pharmaceutical composition in an amount in a range of about 1.0 mg to about 10.0 mg.

2. The method of claim 1, wherein each of the metronidazole, clotrimazole, and chlorhexidine is added to the pharmaceutical composition as a salt.

3. The method of claim 1, wherein the pharmaceutical composition is formulated as a suppository pharmaceutical dosage form.

4. The method of claim 1 wherein the pharmaceutical composition is administered once or twice a day, or once every 2 or 3 or 4 days to the patient in a suppository pharmaceutical dosage form.

5. The method of claim 1, wherein the pharmaceutical composition is administered for a period of at least 1 week.

6. The method of claim 1, wherein the pharmaceutical composition is formulated as an enema pharmaceutical dosage form.

7. The method of claim 1, wherein the pharmaceutical composition is dissolved in a solution prior to contact administration of the pharmaceutical composition to treat the hemorrhoid.

8. The method of claim 1, further comprising pre-heating of the hemorrhoid prior to administration of the pharmaceutical composition.

9. The method of claim 8, wherein the pre-heating comprises exposure of the hemorrhoid to infrared light.

10. The method of claim 8, wherein the pre-heating comprises exposure of the hemorrhoid to water at a temperature above a body temperature of the patient.

11. The method of claim 1, further comprising administering the composition to the patient in both a solid form and in a liquid form.

12. The method of claim 11, wherein the solid form is formulated as a suppository pharmaceutical dosage form.

13. The method of claim 11, wherein the liquid form is formulated as an enema pharmaceutical dosage form.

\* \* \* \* \*